(12) United States Patent
Wills et al.

(10) Patent No.: US 11,103,367 B2
(45) Date of Patent: Aug. 31, 2021

(54) ACETABULAR LINER

(71) Applicant: Encore Medical, L.P., Austin, TX (US)

(72) Inventors: Kevin Michael Wills, Austin, TX (US); Adam Shallenberg, Austin, TX (US)

(73) Assignee: Encore Medical, L.P., Austin, TX (US)

( * ) Notice: Subject to any disclaimer, the term of this patent is extended or adjusted under 35 U.S.C. 154(b) by 0 days.

(21) Appl. No.: 16/782,721

(22) Filed: Feb. 5, 2020

(65) Prior Publication Data

US 2020/0261248 A1 Aug. 20, 2020

Related U.S. Application Data

(60) Provisional application No. 62/806,589, filed on Dec. 15, 2019.

(51) Int. Cl.
*A61F 2/34* (2006.01)
*A61F 2/46* (2006.01)

(52) U.S. Cl.
CPC .............. *A61F 2/4684* (2013.01); *A61F 2/34* (2013.01)

(58) Field of Classification Search
CPC ...... A61F 2/34; A61F 2/4684; A61F 2/30767; A61F 2/32; A61F 2/4609; A61F 2/4637; A61F 2002/30329; A61F 2002/30331; A61F 2002/30352; A61F 2002/30367; A61F 2002/30476; A61F 2002/30484; A61F 2002/30487; A61F 2002/305; A61F 2002/30579; A61F 2002/30594; A61F 2002/30604; A61F 2002/30616;
(Continued)

(56) References Cited

U.S. PATENT DOCUMENTS

| | | |
|---|---|---|
| 5,725,591 A | 3/1998 | DeCarlo et al. |
| 6,152,961 A | 11/2000 | Ostiguy et al. |
| 6,475,243 B1 | 11/2002 | Sheldon et al. |

(Continued)

FOREIGN PATENT DOCUMENTS

| | | |
|---|---|---|
| DE | 69200772 T2 | 7/1995 |
| EP | 0 927 548 | 5/2003 |

(Continued)

OTHER PUBLICATIONS

International Search Report and Written Opinion dated Jun. 2, 2020 in application No. PCT/US2020/016994.

*Primary Examiner* — Bruce E Snow
*Assistant Examiner* — Melissa A Hoban
(74) *Attorney, Agent, or Firm* — Knobbe Martens Olson & Bear LLP (57) ABSTRACT

An acetabular liner having a closed first end, an open second end, and a liner wall having a distal peripheral edge. The acetabular liner wall can include an interior surface, an exterior surface configured to be received within an acetabular shell, a first cutout through the liner wall, a second cutout parallel to the first cutout and through the liner wall, and a third cutout in the interior surface partially through the liner wall, the third cutout extending between the first and second cutouts, and at least one movable tab extending from the peripheral edge inwardly towards an axial center of the liner and having sidewalls defined by one of the sets of cutouts, the tab comprising at least one projection on an exterior surface of the tab configured to removably secure to a portion of an acetabular shell.

20 Claims, 6 Drawing Sheets

(58) Field of Classification Search
CPC .. A61F 2002/30827; A61F 2002/30891; A61F 2002/3414; A61F 2002/3429
See application file for complete search history.

(56) References Cited

U.S. PATENT DOCUMENTS

| | | | |
|---|---|---|---|
| 7,169,185 | B2 | 1/2007 | Sidebotham |
| 8,066,778 | B2 | 11/2011 | Meridew et al. |
| 8,585,769 | B2 | 11/2013 | Vankoski et al. |
| 8,679,187 | B2 | 3/2014 | Allen et al. |
| 9,144,497 | B2 | 9/2015 | Sun et al. |
| 9,232,827 | B1* | 1/2016 | Penn ..................... A42B 3/324 |
| 9,463,094 | B2 | 10/2016 | Allen et al. |
| 9,615,927 | B2 | 4/2017 | Huff et al. |
| 9,615,943 | B2 | 4/2017 | Brown et al. |
| 9,629,873 | B2 | 4/2017 | Manuel et al. |
| 9,642,709 | B2 | 5/2017 | Boedo et al. |
| 9,649,202 | B2 | 5/2017 | Behzadi et al. |
| 9,655,725 | B2 | 5/2017 | Bresina et al. |
| 9,662,216 | B2 | 5/2017 | Witt et al. |
| 9,662,228 | B2 | 5/2017 | McCarthy |
| 9,668,745 | B2 | 6/2017 | Komistek |
| 9,730,811 | B2 | 8/2017 | Flohr et al. |
| 9,744,045 | B2 | 8/2017 | Link |
| 9,763,676 | B2 | 9/2017 | Motherway et al. |
| 9,808,345 | B2 | 11/2017 | Grotz |
| 9,814,603 | B2 | 11/2017 | Gradel |
| 9,872,771 | B2 | 1/2018 | Tepic |
| 9,889,224 | B2 | 2/2018 | Oral et al. |
| 9,907,661 | B2 | 3/2018 | Ries |
| 9,913,734 | B2 | 3/2018 | White et al. |
| 9,926,116 | B2 | 3/2018 | Kinyon |
| 9,943,319 | B2 | 4/2018 | Fortin et al. |
| 9,943,993 | B2 | 4/2018 | Muratoglu et al. |
| 9,962,463 | B2 | 5/2018 | Muratoglu et al. |
| 9,968,456 | B2 | 5/2018 | Song |
| 9,993,343 | B2 | 6/2018 | Smith |
| 10,028,846 | B2 | 7/2018 | Flohr et al. |
| 10,064,729 | B2 | 9/2018 | Komistek |
| 10,092,304 | B2 | 10/2018 | Fortin et al. |
| 10,092,404 | B2 | 10/2018 | Hanssen et al. |
| 10,092,419 | B2 | 10/2018 | Hananouchi et al. |
| 10,098,743 | B2 | 10/2018 | Hanssen et al. |
| 2007/0123856 | A1* | 5/2007 | Deffenbaugh ......... A61B 17/15 606/54 |
| 2008/0221666 | A1* | 9/2008 | Licata ..................... A61F 2/95 623/1.22 |
| 2010/0102484 | A1* | 4/2010 | Haney ................. A61F 2/30942 264/328.1 |
| 2010/0161072 | A1* | 6/2010 | Drescher ................... A61F 2/34 623/22.29 |
| 2011/0015753 | A1* | 1/2011 | Meridew .................. A61F 2/34 623/22.24 |
| 2014/0200675 | A1 | 7/2014 | Termanini |
| 2016/0089156 | A1 | 3/2016 | Fortin et al. |
| 2017/0086980 | A1 | 3/2017 | Suckow |
| 2017/0095539 | A1 | 4/2017 | Tan |
| 2017/0095590 | A1 | 4/2017 | Manuel et al. |
| 2017/0107370 | A1 | 4/2017 | Myung et al. |
| 2017/0128626 | A1 | 5/2017 | Shavit |
| 2017/0181857 | A1 | 6/2017 | Wang et al. |
| 2017/0189190 | A1 | 7/2017 | Satterthwaite et al. |
| 2017/0189206 | A1 | 7/2017 | Davenport et al. |
| 2017/0202682 | A1 | 7/2017 | McCarthy |
| 2017/0216037 | A1 | 8/2017 | Huff et al. |
| 2017/0224418 | A1 | 8/2017 | Boettner et al. |
| 2017/0224496 | A1 | 8/2017 | Witt et al. |
| 2017/0224872 | A1 | 8/2017 | Shavit |
| 2017/0296274 | A1 | 10/2017 | van der Walt et al. |
| 2017/0325972 | A1 | 11/2017 | Steif |
| 2017/0348011 | A1 | 12/2017 | Kourtis et al. |
| 2017/0348109 | A1 | 12/2017 | Bird et al. |
| 2017/0367830 | A1 | 12/2017 | Kazanovicz |
| 2018/0042727 | A1 | 2/2018 | Band et al. |
| 2018/0049894 | A1 | 2/2018 | Siccardi et al. |
| 2018/0055656 | A1 | 3/2018 | Gradel |
| 2018/0092745 | A1 | 4/2018 | McAlexander |
| 2018/0125664 | A1 | 5/2018 | Bailey et al. |
| 2018/0140425 | A1 | 5/2018 | Kulber |
| 2018/0193038 | A1 | 7/2018 | Fortin et al. |
| 2018/0194042 | A1 | 7/2018 | Muratoglu et al. |
| 2018/0214233 | A1 | 8/2018 | Termanini et al. |
| 2018/0221154 | A1 | 8/2018 | Smith et al. |
| 2018/0236136 | A1 | 8/2018 | Kourtis et al. |
| 2018/0256337 | A1 | 9/2018 | Hanssen et al. |

FOREIGN PATENT DOCUMENTS

| | | |
|---|---|---|
| EP | 0 941 718 | 6/2004 |
| EP | 1 308 140 | 1/2012 |
| EP | 2 198 808 | 10/2012 |
| EP | 2 007 318 | 7/2013 |
| EP | 2 007 292 | 9/2016 |
| EP | 2 793 757 | 4/2017 |
| EP | 2 744 454 | 5/2017 |
| EP | 2 403 437 | 6/2017 |
| EP | 2 750 632 | 7/2017 |
| EP | 2 976 048 | 8/2017 |
| EP | 1 750 614 | 9/2017 |
| EP | 2 822 512 | 10/2017 |
| EP | 3 235 522 | 10/2017 |
| EP | 2 996 634 | 11/2017 |
| EP | 3 253 322 | 12/2017 |
| EP | 1 384 456 | 1/2018 |
| EP | 3 187 152 | 3/2018 |
| EP | 3 062 746 | 5/2018 |
| EP | 2 967 660 | 10/2018 |
| EP | 3 076 905 | 10/2018 |
| EP | 3 381 413 | 10/2018 |
| EP | 3 283 013 | 10/2019 |
| EP | 3 288 502 | 10/2019 |
| FR | 2684544 | 6/1993 |
| WO | WO 07/108848 | 9/2007 |
| WO | WO 07/121313 | 10/2007 |
| WO | WO 11/008757 | 1/2011 |
| WO | WO 13/032589 | 3/2013 |
| WO | WO 16/014616 | 1/2016 |
| WO | WO 16/053712 | 4/2016 |
| WO | WO 16/102976 | 6/2016 |
| WO | WO 16/160892 | 10/2016 |
| WO | WO 16/169913 | 10/2016 |
| WO | WO 16/205077 | 12/2016 |
| WO | WO 17/024202 | 2/2017 |
| WO | WO 17/027590 | 2/2017 |
| WO | WO 17/034845 | 3/2017 |
| WO | WO 17/053183 | 3/2017 |
| WO | WO 17/073458 | 5/2017 |
| WO | WO 17/077341 | 5/2017 |
| WO | WO 17/097760 | 6/2017 |
| WO | WO 17/123506 | 7/2017 |
| WO | WO 17/127140 | 7/2017 |
| WO | WO 17/151607 | 9/2017 |
| WO | WO 17/214095 | 12/2017 |
| WO | WO 18/004982 | 1/2018 |
| WO | WO 18/009807 | 1/2018 |
| WO | WO 18/013224 | 1/2018 |
| WO | WO 18/063872 | 4/2018 |
| WO | WO 18/075478 | 4/2018 |
| WO | WO 18/085900 | 5/2018 |
| WO | WO 18/149599 | 8/2018 |
| WO | WO 18/169995 | 9/2018 |
| WO | WO 18/183681 | 10/2018 |

* cited by examiner

ACETABULAR LINER

REFERENCE TO PRIORITY APPLICATIONS

This application claims the benefit of U.S. Provisional Application No. 62/806,589 filed on Feb. 15, 2019, and titled "ACETABULAR LINER." The entire disclosure of each of the above items is hereby made part of this specification as if set forth fully herein and incorporated by reference for all purposes, for all that it contains.

Any and all applications for which a foreign or domestic priority claim is identified in the Application Data Sheet as filed with the present application are hereby incorporated by reference under 37 CFR 1.57.

TECHNICAL FIELD

The present disclosure relates to trial acetabular liners. More specifically, the present disclosure includes structural features of a trail acetabular liner.

BACKGROUND

A background is provided for introductory purposes and to aid the reader in understanding the detailed description. The background should not be taken as an admission of any prior art to the claims.

In total hip replacement surgery, prosthetic implants are used to replace the acetabulum and femoral head of the hip joint. The acetabulum can be replaced with an acetabular cup. The acetabular cup can include an outer acetabular shell and an acetabular liner configured to receive a prosthetic femoral component. Prior to implantation of the final liner, one or more trial liners can be inserted into their the trial or final cup to test the fit to the body.

Traditional trial liners often include a plastic component that mimics the shape of the final liner but does not include the locking mechanism used to secure the final liner to the final shell. A trial liner generally includes cup-like liner that has a closed end, an open end, and a liner wall extending between the closed end and the open end. The interior surface of the liner wall can define a chamber configured to receive a prosthetic femoral component. The trail liner exterior surface of the liner wall is configured to be received within the shell. Once the trail liner is inserted properly into the cup, it can be difficult to remove due to the tight fit and restrictive working environment. Accordingly, it would be advantageous to have a trail liner that can fit tightly and properly into a cup for fitting purposes, but is also easier to remove from the cup.

SUMMARY

This disclosure describes various embodiments of a trial acetabular liner, and examples of various features that can be included in the various embodiments.

One innovation includes a trial acetabular liner. The trial acetabular liner can be characterized as having (or defining) perpendicular radial and axial directions. The trial acetabular liner can include a closed first end, an open second end, and a liner wall extending between closed first end and the open second end, the liner wall having a distal peripheral edge defining an outside perimeter of the open second end. The liner wall can include an interior surface defining a chamber for receiving a femoral head component, an exterior surface configured to be received within an acetabular shell, and at least one set of cutouts including a first cutout through a portion of the liner wall, a second cutout parallel to the first cutout and through the liner wall, the first and second cutouts extending from the distal peripheral edge into the interior surface of the liner, and a third cutout in the interior surface of the liner and partially through the liner wall, the third cutout extending from a proximal edge of the first cutout to a proximate edge of the second cutout, the proximate edges of the first and second cutouts nearer a center axis of the liner than the distal peripheral edge. The trial acetabular liner can further include at least one movable tab extending from the distal peripheral edge towards the center axis of the liner, each tab having sidewalls defined by one of the at least one set of cutouts, and each tab comprising at least one projection on an exterior surface of the tab configured to removably secure to a portion of an acetabular shell.

Various aspects of implementations can include one or more of other features described herein. In some implementations of an acetabular liner, the least one projection includes a first projection and a second projection. In some implementations of an acetabular liner, the at least one tab further comprises a first indentation in the distal peripheral edge on the tab, the first indentation extending in the axial direction towards the closed first end from a first end of the first indentation on the distal peripheral edge to a second end of the first indentation proximate to the first and second projections. In some such implementations, the first indentation defines a side portion of the first projection and a side portion of the second projection. In some implementations of an acetabular liner, the liner includes a first movable tab and a second movable tab, the first movable tab and the second movable tab aligned opposite each other. In some such implementations, the at least one set of cutouts comprises a first set of cutouts associated with the first moveable tab and a second set of cutouts associated with the second moveable tab. In some such implementations, the at least one tab further comprises a liner wall groove beginning near the second end of the first indentation and extending towards the closed first end of the liner. In some implementations, the liner wall groove is separate from the first indentation. In some implementations, the liner wall groove is separated from the first indentation by an edge at the second end of the first indentation. In some implementations of the acetabular liner, the at least one tab further includes a second indentation extending axially from near the second end of the first indentation towards the first closed end of the liner, the second indentation being indented less than or the same amount as first indentation. In some implementations of the acetabular liner, the first indentation extends past the at least one projection. In some implementations of the acetabular liner, the first indentation is structured to receive a surface of a tool, and wherein the tab is configured to move inwardly in a direction towards an axis of the liner when force is applied to the first indentation by the tool. In some implementations of the acetabular liner, the first indentation is structured to receive a surface of a finger, and wherein the tab is configured to move inwardly in a direction towards axis of the liner when force is applied to the first indentation by the finger. In some implementations of the acetabular liner, the third cutout is aligned perpendicular to the first and second cutouts.

Another innovation is a trial acetabular liner for use in determining an implantable liner to use for replacement of a hip joint that includes a closed first end, an open second end, and a liner wall extending between closed first end and the open second end. The liner wall can include an interior surface and an exterior surface, at least one set of cutouts including a first cutout through the liner wall, a second cutout through the liner wall, and a third cutout in the interior surface of the liner wall partially through the liner wall extending from the first cutout to the second cutout. The trial acetabular liner can further include at least one movable tab extending from the peripheral edge inwardly towards an axial center of the liner and having sidewalls defined by one of the at least one set of cutouts, the tab comprising at least one projection on an exterior surface of the tab configured to removably secure to an indentation of an acetabular shell.

Various aspects of implementations can include one or more of other features described herein. In some implementations of a trial acetabular liner, the at least one projection comprises a first projection and a second projection. In some implementations of a trial acetabular liner, the at least one tab further comprises a first indentation in the distal peripheral edge on the tab, the indentation extending in the axial direction towards the closed first end from a first end of the first indentation on the distal peripheral edge to a second end of the first indentation proximate to the first and second projections. In some implementations of a trial acetabular liner, the first indentation defines a side portion of the first projection and a side portion of the second projection. In some implementations of a trial acetabular liner, the at least one moveable tab comprises a first movable tab and a second movable tab disposed opposite each other. In implementations of a trial acetabular liner, the at least one set of cutouts comprises a first set of cutouts associated with the first moveable tab and a second set of cutouts associated with the second moveable tab. In some implementations of a trial acetabular liner, the at least one tab further comprises a liner wall groove beginning near the second end of the first indentation and extending towards the closed first end of the liner. In some implementations, the liner wall groove is separate from the first indentation. In some implementations, the liner wall groove is separated from the first indentation by an edge at the second end of the first indentation. In some implementations, the at least one tab further includes a second indentation extending axially from near the second end of the first indentation towards the first closed end of the liner, the second indentation being indented less than or the same amount as first indentation. In some implementations, the first indentation extends past the at least one projection. In some implementations of a trial acetabular liner, the first cutout is parallel to the second cutout. In some implementations of a trial acetabular liner, the third cutout is perpendicular to the first cutout and the second cutout. In some implementations of a trial acetabular liner, the third cutout is curved. In some implementations of a trial acetabular liner, the first cutout and the second cutout are curved. In some implementations of a trial acetabular liner, the first cutout is not parallel to the second cutout. In some implementations of a trial acetabular liner, the third cutout is not perpendicular to the to the first cutout.

Another innovation is a trial acetabular liner assembly defining perpendicular radial and axial directions, the trial acetabular liner assembly including an acetabular shell and a liner, The liner can includes a closed first end, an open second end, and a liner wall extending between closed first end and the open second end, the liner wall having a distal peripheral edge defining an outside perimeter of the open second end. The liner includes an interior surface defining a chamber for receiving a femoral head component, an exterior surface configured to be received within an acetabular shell, at least one set of cutouts including a first cutout through a portion of the liner wall, a second cutout parallel to the first cutout and through the liner wall, the first and second cutouts extending from the distal peripheral edge into the interior surface of the liner, and a third cutout in the interior surface of the liner and partially through the liner wall, the third cutout extending from a proximal edge of the first cutout to a proximate edge of the second cutout, the proximate edges of the first and second cutouts nearer a center axis of the liner than the distal peripheral edge, and the liner further including at least one movable tab extending from the distal peripheral edge towards the center axis of the liner, each tab having sidewalls defined by one of the at least one set of cutouts, and each tab comprising at least one projection on an exterior surface of the tab configured to removably secure to a portion of the acetabular shell.

Various aspects of implementations of the trail acetabular liner assembly can include one or more of other features described herein. For example, the trial acetabular liner can further include the acetabular shell, the acetabular shell comprising an inner surface having a groove configured to receive the at least one projection. In some implementations, the inner surface of the acetabular shell further comprises at least one an indentation for receiving a locking portion of an implantable acetabular liner. In some implementations, the at least one projection on the exterior surface of the depressible tab is configured to snap-fit with the groove of the acetabular shell. In some implementations, the at least one projection comprises a first projection and a second projection, where the first and second projections on the exterior surface of the depressible tab are configured to snap-fit with the groove on the inner surface of the acetabular shell.

BRIEF DESCRIPTION OF THE DRAWINGS

The features and advantages of the devices described herein will become more fully apparent from the following description and appended claims, taken in conjunction with the accompanying drawings. These drawings depict only several embodiments in accordance with the disclosure and are not to be considered limiting of its scope. In the drawings, similar reference numbers or symbols typically identify similar components, unless context dictates otherwise. In some instances, the drawings may not be drawn to scale.

DETAILED DESCRIPTION OF CERTAIN INVENTIVE ASPECTS

The following detailed description is directed to certain aspects and examples of the invention. However, the invention can be embodied in a multitude of different ways. It should be apparent that the aspects herein may be embodied in a wide variety of forms and that any specific structure, function, or both being disclosed herein is merely representative of one or more embodiments of the invention. An aspect disclosed herein may be implemented independently of any other aspects and that two or more of these aspects may be combined in various ways. For example, different embodiments of an acetabular trial liner may be implemented using any number of the aspects/features disclosed herein. In addition, such a device may be implemented or such a method may be practiced using other structure, functionality, or structure and functionality in addition to, or other than one or more of the aspects set forth herein.

In total hip replacement surgery, prosthetic implants are used to replace the acetabulum and femoral head of the hip joint. The acetabulum can be replaced with an acetabular cup. The acetabular cup can include an outer acetabular shell and an acetabular liner configured to receive a prosthetic femoral component. Prior to implantation of the final liner, one or more trial liners can be inserted into their the trial or final cup to test the fit to the body.

Traditional trial liners often include a plastic component that mimics the shape of the final liner but does not include the locking mechanism used to secure an implantable liner in an acetabular shell. Examples of a trial liner can include a closed first end, an edge defining an open second end, and a liner wall extending between the closed first end and the open second end. The interior surface of the liner wall can define a chamber configured to receive a prosthetic femoral component. An exterior surface of the liner wall is configured to be received within a shell. The liner wall may include an interior surface, an exterior surface, at least one set of cutouts that define a portion of at least one movable tab.

The at least one movable tab can include structure that removably secures the trial liner to the shell without the use of an additional fastener (such as a screw or other similar type of mechanical fastener as is common with implantable liners). In some embodiments, each tab can include an articulating structure configured to engage the shell to secure the trial liner in place, via for example, a snap-fit. In some embodiments, an edge of the tab is configured to be inset a distance from the outside edge of the liner, providing a place for a user to contact the tab to move the tab inward, thus unlocking a projection of the tab from a shell that the liner is locked into. In different embodiments, there may be one or more movable tabs formed in the side surfaces of a trial liner. Examples of certain features that can be included in embodiments of a trial acetabular liner are described below in reference to FIGS. 1-8.

Figure 1:
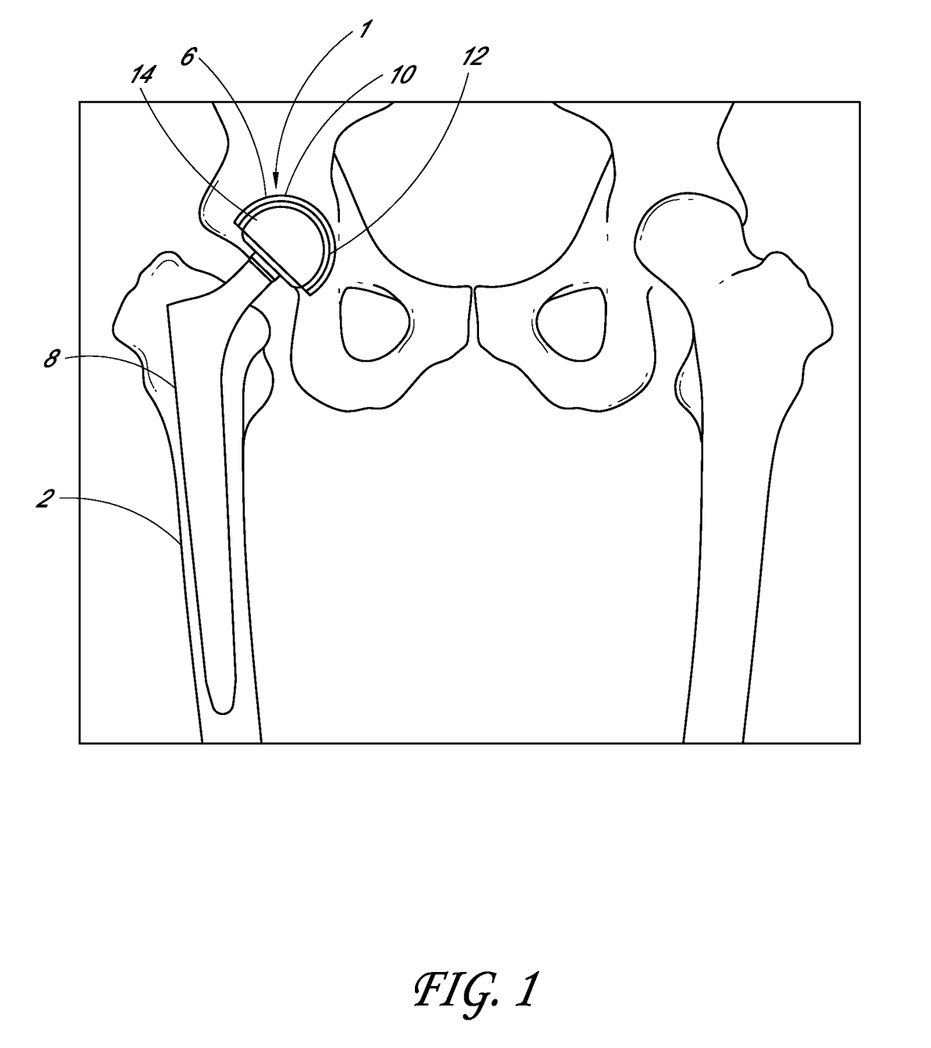
FIG. 1 is an illustration of an example of an implanted hip replacement system.

The following is a list of certain components that are described and enumerated in this disclosure in reference to the above-listed figures. However, any aspect illustrated in the figures, whether or not called out separately herein, can form a portion of various embodiments of the invention and may provide basis for claim limitation relating to such aspects, with or without additional description. The enumerated components include:

1 acetabulum
2 femur
6 acetabular component
8 femoral component
10 acetabular shell
12 acetabular liner
14 femoral head
18 open second end of the liner
19 closed first end of the liner
22 tab
24 distal peripheral edge of the liner
26 interior surface of the liner
28 projection
29 projection
30 top surface on liner
32 indentation
33 inner peripheral edge of liner
34 cutouts along tab
36 lateral wall
38 third cutout
39 second indentation
40 proximal end indentation
42 distal end indentation
44 edge of indentation
46 groove in liner
48 groove in shell
50 alignment protrusions
52 alignment recesses
54 liner wall
55 interior of liner
56 interior surface of shell
57 exterior surface liner wall
58 exterior surface of shell
60 proximal end cutout
61 distal end cutout
62 distal wall of tab defined by third cutout
66 open end of shell
68 closed end of shell
70 proximal wall defined by third cutout
71 locking feature
80 outside edge of tab
82 inside edge of tab FIG. 1 illustrates a schematic of an example of system implanted into a femur 2 and an acetabulum 1 of a patient. In hip replacement surgery, prosthetic implants may be used to replace the acetabulum and femoral head of the hip joint. The acetabulum can be replaced with an acetabular component 6. The acetabular component 6 (or "cup") can include an outer acetabular shell 10 (sometimes referred to herein as a "shell") and an acetabular liner 12 (sometimes referred to herein as a "liner"). The liner 12 is configured to receive a prosthetic a femoral head 14 of a femoral component 8. Prior to implantation of the acetabular component 6, one or more trial acetabular shells 10 can be inserted into the patient to test the fit to the patient's acetabulum 1. While a trial acetabular shell 10 is positioned within the acetabulum 1, one or more trial liners 12 can inserted into the trial acetabular shell to test the fit to the patient's acetabulum 1, the range of motion of the joint, etc. before insertion of a final acetabular shell and a final acetabular liner. A trial acetabular liner 12 can be used in a shell 10 disposed in the acetabulum 1 and the range of motion and stability using the trial acetabular liner and corresponding components can be assessed. If the trial acetabular liner 12 and corresponding components provides a desired range of motion and stability, the final components can be implanted. If the trial acetabular liner 12 and the corresponding components do not provide the desired range of motion and stability, the trial acetabular liner and/or another component can be removed and replaced with additional trial components bodies until the desired components are found.

A trial acetabular liner 12 may be a component that is similar to the shape and structure of a final acetabular liner (i.e. which ultimately is implanted in a patient) but the trial liner 12 does not include a relatively "permanent" locking mechanism that may be as used to secure the final acetabular liner to the final acetabular shell for long term use in a patient. Instead, the trial acetabular liner includes a "temporary" locking mechanism that locks the trial acetabular liner 12 into the shell 10 for a short period of time for fitting purposes and allows easy and quick removal of the trial acetabular liner 12.

Figure 2:
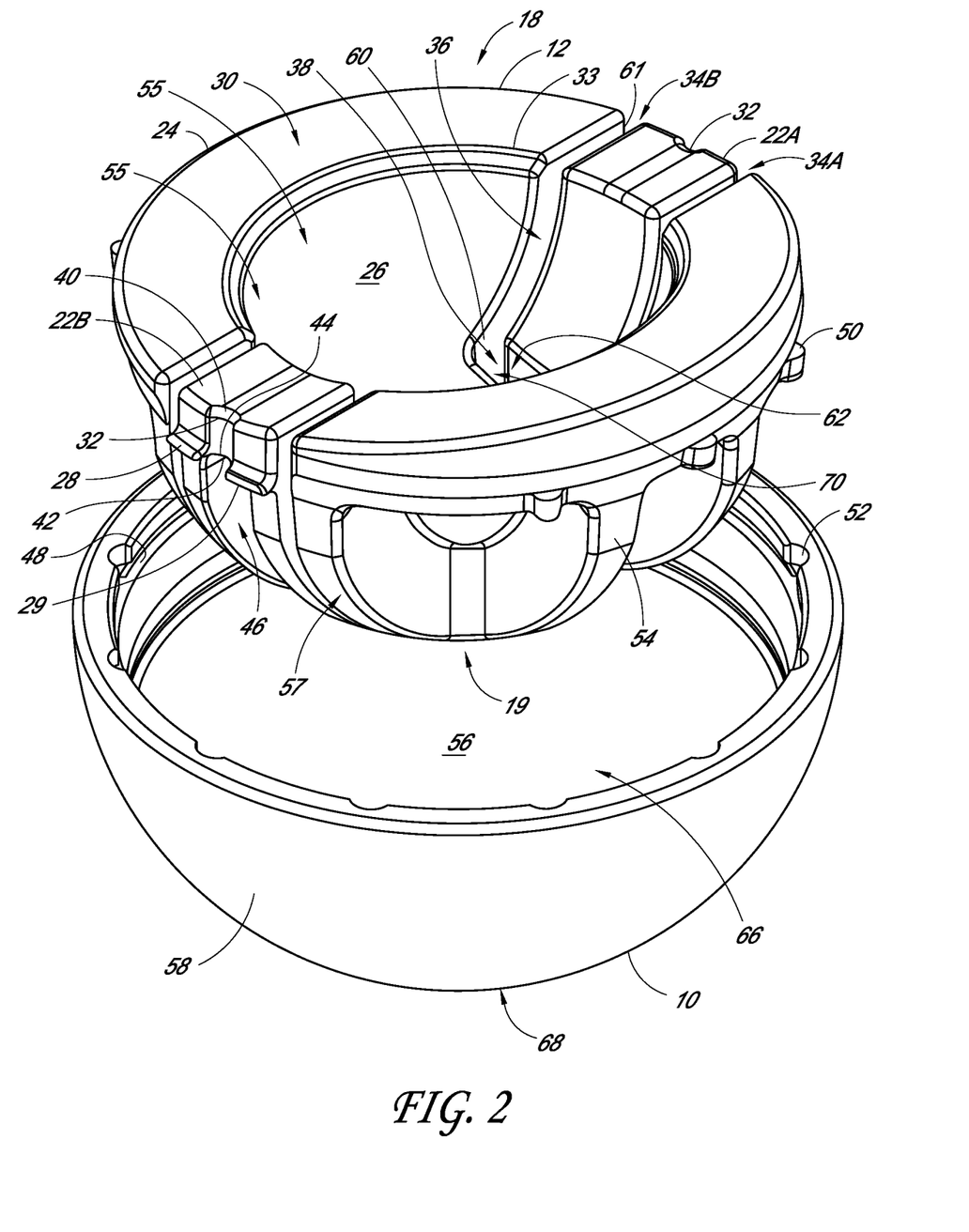
FIG. 2 is an exploded view illustration of an embodiment of an acetabular cup assembly that includes a trial acetabular liner and an acetabular shell.

FIG. 2 is an illustration of an embodiment of an acetabular cup assembly that includes a trial acetabular liner 12 and an acetabular shell 10. The illustrated embodiment of the liner 12 includes a closed first end 19, a distal peripheral edge 24 defining an edge of the open second end 18, and an exterior liner wall 54 extending between the closed first end 19 and the open second end 18. The liner 12 has an interior 55. An interior surface 26 of the liner 12, disposed opposite of the exterior liner wall 54, defines an interior portion 55 (e.g., a chamber or cavity) of the liner 12 which is configured to receive a prosthetic femoral component, and is correspondingly shaped for such a component. For example, various corresponding prosthetic femoral components may have different shapes to address different problems, and the interior surface 26 can be structured to correspond with the particular femoral head component being used. In some examples, the interior surface 26 of the liner 12 may be generally hemispherical in shape. The interior of the shell 10, e.g., defined by the interior surface 56, is configured to receives the liner 12. The exterior liner wall 54 is configured to be received within the shell 10 such that the interior surface 56 of the shell 10 is positioned proximate to the exterior liner wall 54. The shell 10 includes an open end 66 and a closed end 68. The exterior surface 58 of the shell 10 is often configured for bone ingrowth to anchor the shell 10 in the acetabulum.

FIG. 2 illustrates a number of additional aspects of the illustrated embodiments of the shell 10 and the liner 12. The liner 12 includes a distal peripheral edge 24 along the outer perimeter of the open end 18 of the liner 12. A top surface 30 on the open end 18 of the liner 12 extends from the distal peripheral edge 24 generally in a plane inwardly to the inner peripheral edge 33 that is adjacent to the top portion of the inside surface 26. A liner wall 54 extends from the top surface 30 (e.g., the open end 18) to the closed end 19. The liner wall 54 includes the interior surface 26 and the exterior surface 57.

Both the interior surface 26 and the exterior surface 57 of the liner wall 54 include various structures to facilitate the use of the liner 12. The inside surface 26 is generally smooth to accommodate a femoral component, for example, a femoral head. A set of three cutouts define portions of one or more tabs 22 that are movable, the tabs 22 having structures thereon that couple to a corresponding structure of the shell 10, and that can hold the liner 12 in the shell 10. The structures on the tabs 22 and the corresponding structure of the shell 10 can be sized and shaped in various configurations, the embodiment illustrated in FIG. 2 being one example. In another example, the tables 22 may include one or more protrusions that fits into corresponding apertures or holes on the shell 10.

The tabs 22 of the liner 12 illustrated in FIG. 2 includes two tabs, tab 22A and tab 22B. Both tabs 22A, 22B may sometimes be referred to herein as tabs 22 for ease of reference. The liner 12 includes cutouts that define a portion of the tabs. For example, a separate set of three cutouts can be associated with each tab 22, and the three cutouts can define portions of each tab 22, e.g., certain lateral walls/surfaces of the tab 22, as illustrated in FIG. 2. For the two tabs 22A and 22B illustrated in FIG. 2, there are two sets of cutouts, where one set of cutouts is associated with each of the two tabs 22A, 22B. As an example, one set of cutouts 34A, 34B and 38 define sides of tab 22A, and extend through a portion of the inside surface 26.

In the illustrated embodiments, cutouts 34A, 34B are each planar, or substantially planar, in shape and extend in parallel in an axial direction from the open and top surface 30 towards the closed end 19. Cutouts 34A, 34B extend completely through a portion of the liner wall 54, e.g., from the distal peripheral edge 24 inward into the interior of the liner 12. In this way, cutouts 34A, 34B define lateral walls of tab 22 that extend in planes generally in an axial direction.

The cutouts 34A, 34B also define lateral walls 36 in the liner wall 54. Cutout 34A, because of the absence of liner material in the cutout 34, defines a lateral wall on the side of the tab 22 and a (parallel) lateral wall of the liner wall 54. Cutout 34B, as a result of the absence of liner material in the cutout 34, defines a lateral wall on the side of the tab 22, and defines a lateral wall of the liner wall 54 that is parallel to the lateral wall on tab 22. The cutouts 34A, 34B extend from a cutout distal end 61 at the distal peripheral edge 24 into the liner to a cutout proximal end 60 at a point (and edge) of the liner inside surface 26.

The third cutout 38 in the set of cutouts associated with tab 22A extends through a portion of the liner wall 54, forming a cutout in the interior surface 26. Cutout 38 extends between the proximal end 60 of cutouts 34A and 34B, that is, the end of the cutouts 34A and 34B that is closest to a center axis of the liner 12). While cutouts 34A, 34B define cutout portions of the liner 12 that run completely through a portion of the liner wall 54, cutout 38 extends from the inside surface 26 partially into the liner wall 54 but does not extend all the way through the liner wall 54.

In some embodiments including the illustrated embodiment, the orientation of cutout 38 is aligned perpendicular to cutouts 34A and 34B. In some embodiments, cutout 38 is aligned at an angle to cutouts 34A, 34B (e.g., not perpendicular to the cutouts 34A, 34B). In some embodiments, cutout 38 is not straight. For example, cutout 38 may be curvilinear. In some embodiments, cutout 38 includes two or more sections, where each of the sections are curved or straight. In some embodiments, cutout 38 extends from a proximal end 60 of cutout 34B to a proximal end 60 of cutout 34A.

Cutout 38 defines a distal wall 62 of tab 22, the distal wall 62 facing inward towards an axis of the liner 12 and towards an opposite proximal wall 70 of the liner 12 also defined by cutout 38. By configuring the liner 12 such that cutout 38 extends partially through the liner wall 54, the portion of the liner wall 54 adjacent to cutout 38 (that is not removed) is attached to the tab 22 and allows the tab 22 to move (or flex) such that a top portion of tab 22 (e.g., adjacent to the open and top surface 30) can be moved towards the axis of the liner 12 to detach the trial liner 12 from the shell 10. That is, the tab 22 can be moved such that the distal wall 62 moves towards the opposed distal lateral wall 70.

Cutout 38 thus provides a cavity into which a portion of tab 22 can move to detach the trial liner 12 from the shell 10. This is one improvement of the illustrated embodiment of the trial liner 12 over previous trial liners that may have a tab but such tabs are more difficult to move because of the lack of the gap (cutout 38), often requiring tools that would engage cavities on the tabs in order to obtain a strong enough seat for the tool to operate the tab to release the trial liner from the shell.

As illustrated in FIG. 2, the liner 12 further includes a plurality of alignment protrusions 50 aligned in a plane along the exterior 57 of the liner wall 54. The shell 10 includes alignment recesses 52 that correspond in arrangement to the plurality of alignment protrusions 50 and are shaped and sized to receive the plurality of alignment protrusions 50 when the liner 12 is seated into the shell 10.

Still referring to FIG. 2, in various embodiments, the liner 12 may include one tab 22, two tabs, three tabs, or more than three tabs. The embodiment illustrated in FIG. 2 includes two tabs, a first tab 22A and a second tab 22B. Each tab 22 is formed as a portion of the liner wall 54 and is at least partially defined by three cutouts. For example, tab 22A is partially defined by cutouts 34A, 34B, and 38. A tab 22 may include one or more projections (e.g., projections 28, 29, illustrated on tab 22B) which are received in a groove 48 disposed on the interior surface 56 of the shell 10. The groove 48 may be in a plane that is aligned perpendicular to an axis of the shell 10. When the liner 12 is placed into the shell 10, the projections 28, 29 on each of the tabs 22 are received in the groove 48, locking the liner 12 into the shell 10. The liner 12 may be detached from the shell 10 by moving tabs 22's such that the projections 28, 29 are removed out of the groove 48, allowing the liner 12 to be moved out of the open end 66 of the shell 10.

In the embodiment illustrated in FIG. 2, each tab 22 includes an indentation 32 that extends from an indentation proximal end 40 along the distal peripheral edge 24 in an axial direction towards the closed end 19 of the liner 12, to an indentation distal end 42. In some embodiments, the indentation 32 may run between two projections (e.g., projections 28, 29) on the tab 22. In some embodiments include in the embodiment illustrated in FIG. 2, the indentation distal end 42 is adjacent to the projections 28, 29. In other embodiments, the indentation distal end 42 extends past the projections 28, 29. In the illustrated embodiment, an indentation edge 44 on the tab 22 at the indentation distal end 42 is the end of the indentation 32. In other words, indentation 32 does not extend past the indentation edge 44.

In some embodiments, the tab 22 includes a groove 46, the groove 46 being an open area, for example, a portion of the liner wall 54 that is devoid of structure. In some embodiments, the groove 46 is configured to fit into a corresponding structure in the shell 10. In some embodiments, the groove 46 is designed to minimize the amount of material needed to form a portion of the tab 22/liner wall 54. The tab 22 can be configured to have less material because of the inclusion of the third cutout 38, which allows the tab 22 to be tightly secured into the shell 10 and easily move (due to the gap created by the third cutout 38) to release the liner 12 from a locked position in the shell 10. Such a configuration facilitates the flex or movement of the tab 22 and thus may cause less stress on the material of the liner 12 coupled to the tab 22, and correspondingly the liner 12 may need less material in the tab 22 portion to provide sufficient support and strength so the tab 22 will not break when it is moved.

Figure 3:
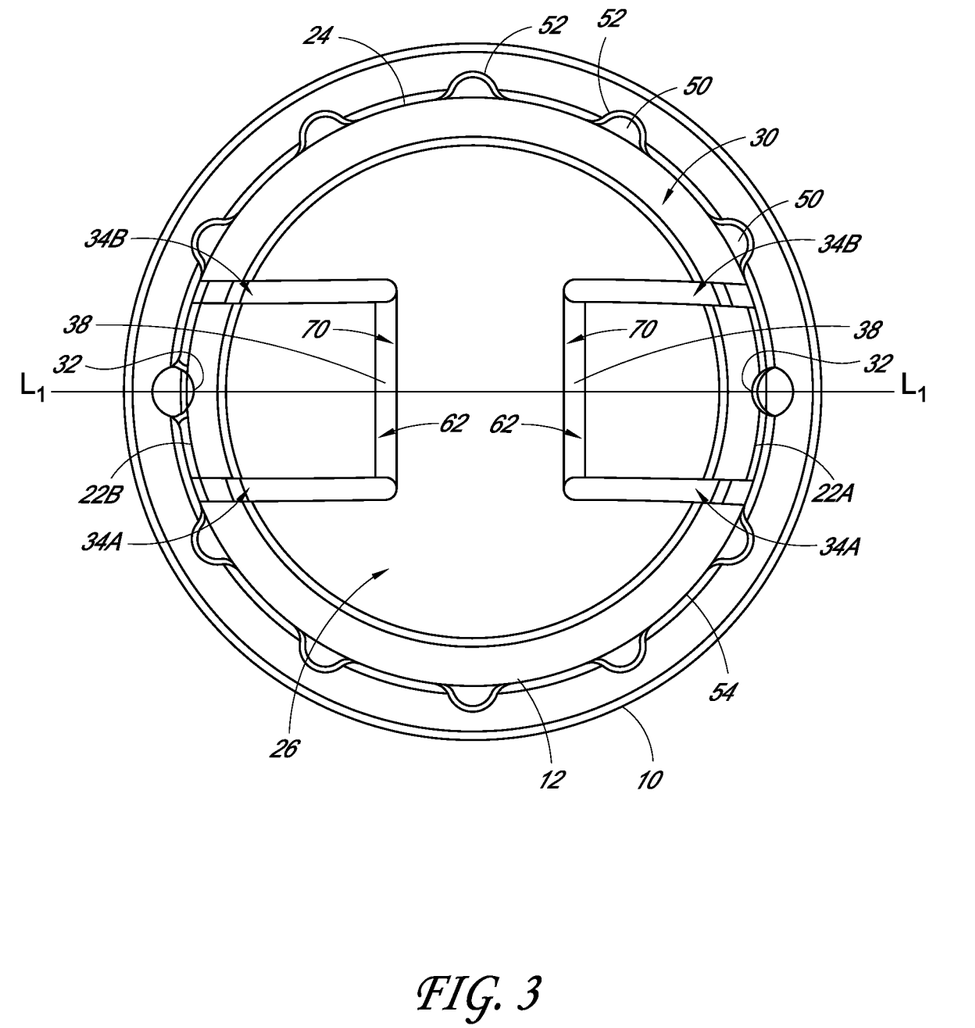
FIG. 3 depicts a plan view of an open end of an embodiment of an acetabular liner and cup assembly.

FIG. 3 depicts a plan view of the open end of the example of the acetabular liner 12 illustrated in FIG. 2 attached to the shell 10. In this view, the two oppositely arranged tabs 22 are shown, each tab 22 being partially defined by a set of cutouts, the set of cutouts having a first cutout 34A, a second cutout 34B that is aligned parallel to the first cutout 34A, and a third cutout 38 that is aligned perpendicular to the first cutout 34A and the second cutout 34B. The first and second cutouts 34A, 34B extend through the liner wall 54. The third cutout 38 extends from the liner interior surface 26 partially through the liner 12. The third cutout 38 defines a distal wall 62 of the tab 22 and the parallel proximal wall 70 of the liner.

FIG. 3 also illustrates the indentation 32 on each of the two tabs 22. The indentation 32 is a structural feature that can be used to move (or depress) the tab 22, for example, by a user's fingers or a tool placed on the indentation 32. To remove the liner 12 from the shell 10, a tool can be placed on one or both of the (oppositely arranged) indentations 32 and the tabs 22 can be moved to release a projection 28, 29 on the tab 22 from the projection 28, 29 receiving groove 48 of the shell 10 (FIG. 2). For example, a tool (or fingers) can move an upper portion of the tabs 22 towards each other (e.g., inward towards the center of the liner 12) to release a projection 28, 29 on the tab 22 from the projection 28, 29 receiving groove 48 of the shell 10.

In some configurations, including the configurations illustrated in FIGS. 2 and 3, the third cutout 38 provides a gap that the tab 22 can move through to more easily release the projections from a receiving groove. This is a significant improvement on another configuration that does not have the third cutout 38 where the release of a tabular structure (or projection) may be performed by flexing the material of the tabular structure tabular structure such that there is enough movement for the tabular structure to release from a locking mechanism in a shell. With the illustrated design, fingers or a simple tool may be used in conjunction with the indentation 32 to release the tabs 22 from the locking mechanism with the shell 10, and this obviates the need for using a tool that needs to extend past the upper portion of the tab and be secured in additional structure on the tab in order to provide enough force to release the tabs. Here for example, a tool or a user's fingers can be employed to easily move even just one of the tabs and thus release a locking mechanism (e.g., projections 28, 29) on the tab 22 from a locking mechanism feature (e.g., projection receiving groove 48) on the interior of the shell 10, thereby allowing the liner 12 be removed from the shell 10.

Figure 4:
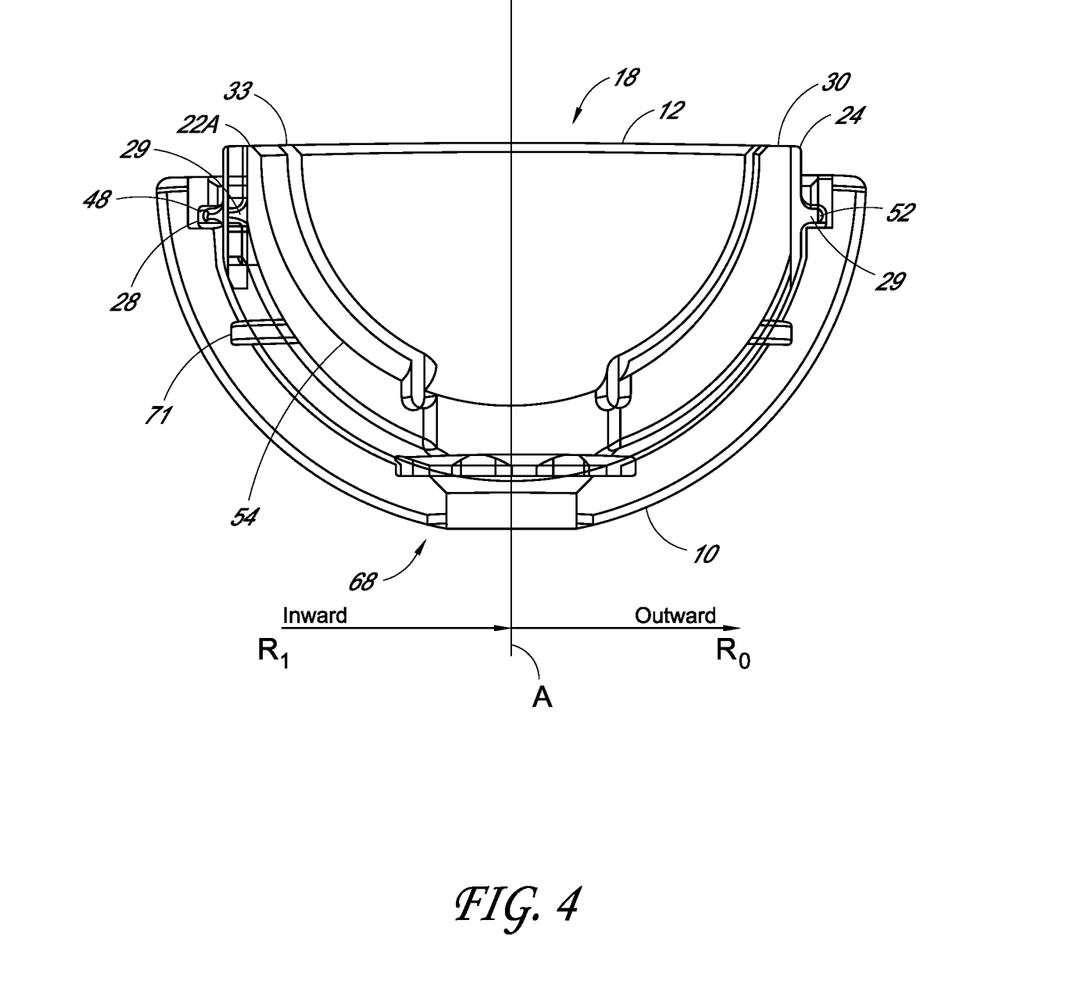
FIG. 4 depicts a cross-sectional view of the example of the acetabular liner and cup assembly of FIG. 3 along line L1-L1.

FIG. 4 depicts a cross-sectional view of the example of the acetabular liner of FIG. 3 along line L1-L1. In reference to the terms "axis," axial," "inward," "inner," and "outer," and "outward" that are used herein, FIG. 4 illustrates in axis A of both the liner 12 in the shell 10, the axis A being perpendicular to the open and top surface 30 of the liner 12 in running through a center point of the liner 12 and the shell 10, and also illustrates the "inward" radial direction $R_I$, and the "outward" radial direction $R_O$.

In FIG. 4, the closed end of the liner 12 is shown as being placed into the open end of the shell 10, and the liner 12 is seated in the interior of the shell 10. As described above, the shell 10 includes a projection receiving groove 48 on an interior wall of the shell 10. In some embodiments, the shell 10 includes one or more projection receiving indentations (or recesses) instead of, or in addition to, the projection receiving groove 48, to receive a projection on the outer liner wall 54 of the liner 12, for temporarily locking the liner 12 into the shell 10, for permanently (e.g., for a longer time than during a fitting process) locking the liner 12 into the shell 10, and or for aligning the liner 12 with the shell 10. The shell 10 may have one or more locking structures 71 (e.g., a groove or recess) that can be used to lock an acetabular implant liner into acetabular shell 10 when the acetabular cup assembly is "permanently" implanted into a patient.

As illustrated in FIG. 4, the projection receiving groove 48 has received a projection 28 associated with the first tab 22 on one side of the shell 10, and a projection 29 associated with a second tab 22 on the opposite side of the shell 10. In this configuration of the shell 10 in the liner 12, the projections 28, 29 enter the projection receiving groove 48 such that they have a "snap-fit" into the projection receiving groove 48. That is, as the liner 12 is placed into the shell 10, the tabs 22 on opposite sides of the liner 12 move inward a small amount as the projections 28, 29 touch the inside wall of the shell 10. The inward movement of the tabs 22 is facilitated by the cutouts 34A, 34B, 38, and in particular cutout 38 as this provides a gap for the tabs 22 to move inward. When the liner 12 is seated correctly in shell 10, the projections 28, 29 move outward into the projection receiving groove 48 temporarily locking the liner 12 into the shell.

In this embodiment, and is also shown in FIG. 2, each tab 22 includes two projections 28, 29. In other embodiments, a tab 22 may be configured to have a single projection, or more than two projections that lock the liner 12 into the shell 10. In the illustrated configuration, each tab 22 has two projections 28, 29 that are separated by the indentation 32. This arrangement (including the third cutout 38) allows the easy movement of the tabs 22 using a simple tool or even one's finger. Other trial acetabular liners may be required to have additional structure (for example, a tool receiving cavity) below the indentation that allows a heavier duty tool to be employed to attach to the tabs and apply enough force to flex the liner wall, that makes up portion of the tab, such that the tab can move inward and be released from the shell 10. The illustrated configuration obviates this requirement and makes it easier and quicker to take the trial acetabular liner 12 in an out of the shell 10. As this is performed during surgery, efficiency and speed of removing a trial acetabular liner is critical as it facilitates trying multiple liners to determine the best fit—the illustrated embodiment facilitates efficiency and speed of this process.

Figure 5:
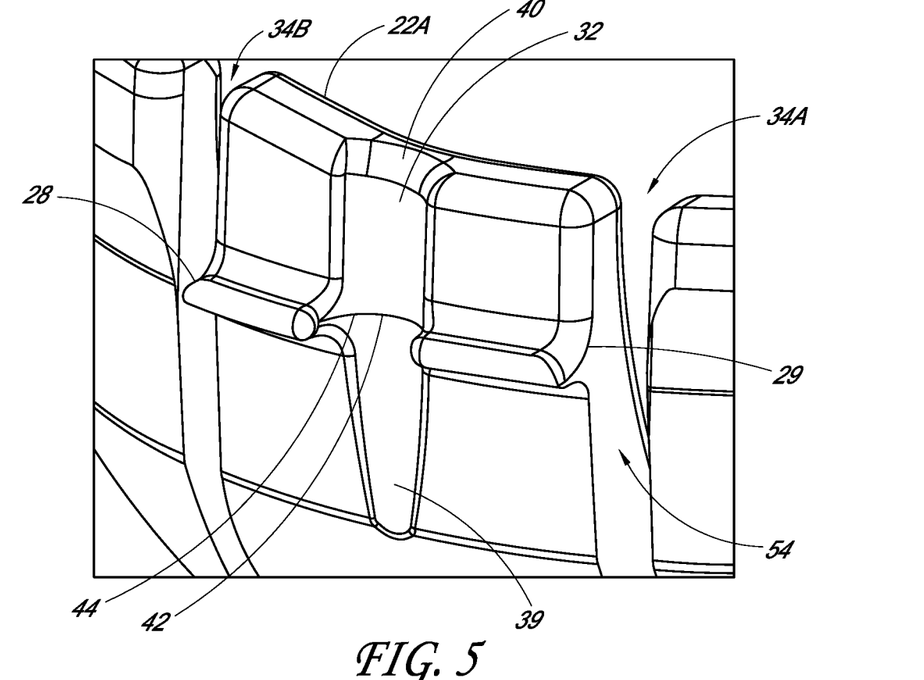
FIG. 5 is perspective view of an illustration of an example of a moveable tab showing a portion of the liner wall having at least one projection (in this example two) on the exterior wall of the tab, where the projections are separated by an indentation that extends in an axial direction between the projections.

FIG. 5 is perspective view of an illustration of an example of a moveable tab 22 showing a portion of the liner wall 54 having at least one projection 28, 29 (in this example two) on the exterior wall of the tab 22, where the projections 28, 29 are separated by an indentation 32 that extends from an indentation proximal end 40 in an axial direction between the projections 28, 29, to an indentation distal end 42. Cutouts 34A, 34B are on opposite sides of the tab 22. In this embodiment, tab 22 includes a second indentation 39 that extends generally in an axial direction from an edge 44 at the distal indentation end 42.

In some embodiments, the second indentation 39 indents inwardly into the liner 12 the same amount, or less than, indentation 32. The edge of indentation 44 may separate the indentation 32 and a second indentation 39. The portion of the tab 22 occupied by the second indentation 39 in the embodiment shown in FIG. 5 may be configured in various ways for example, based on ease of manufacturing or to minimize the liner material necessary to form liner 12. That is, generally the second indentation 39 and the space occupied by the second indentation 39 does not provide required functionality for the tab 22 to operate. Instead, it may provide some structural support (as any material does) that in some embodiments is not necessary or even desired.

Figure 6:
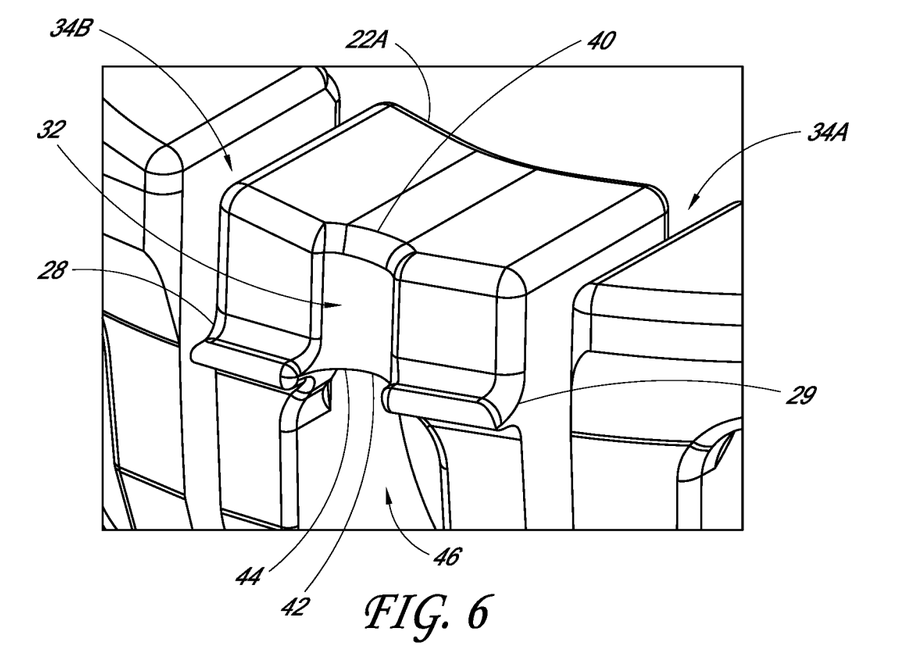
FIG. 6 is perspective view of an illustration of an example of a moveable tab showing a portion of the liner wall having at least one projection (in this example two) on the exterior wall of the tab, where the projections are separated by an indentation that extends in an axial direction between the projections, the tab further including a groove that extends from a portion of the tab proximate to the projections towards the closed end of the liner.

FIG. 6 is perspective view of an illustration of an example of another embodiment, showing a moveable tab 22 showing a portion of the liner wall 54 having at least one projection 28, 29 (in this example two) on the exterior wall of the tab 22. The projections 28, 29 are separated by an indentation 32 that extends in an axial direction between the projections 28, 29. In this embodiment, instead of a second indentation 34 (as illustrated in FIG. 5), in this embodiment tab 22 includes a groove 46 which extends from the edge of the indentation 44 in an axial direction towards the closed and of the liner 12. The groove 46 is an absence of liner material and may be included, for example, as a way to minimize the amount of material needed to manufacture the trial liner 12.

Also, in some embodiments, the groove 46 may be configured to receive a corresponding structure on the inside of a shell, for an alignment or fitting purpose. In some embodiments, such a groove 46 may begin below the edge of indentation 44 and thus is separate and distinct from indentation 32, and the groove 46 spatially and structurally does not communicate with indentation 32. For example, in various embodiments, a line starting at any point in the indentation 32 and moving in an axial direction away from the indentation proximal end 40, the line does not enter or intersect the groove 46.

Figure 7:
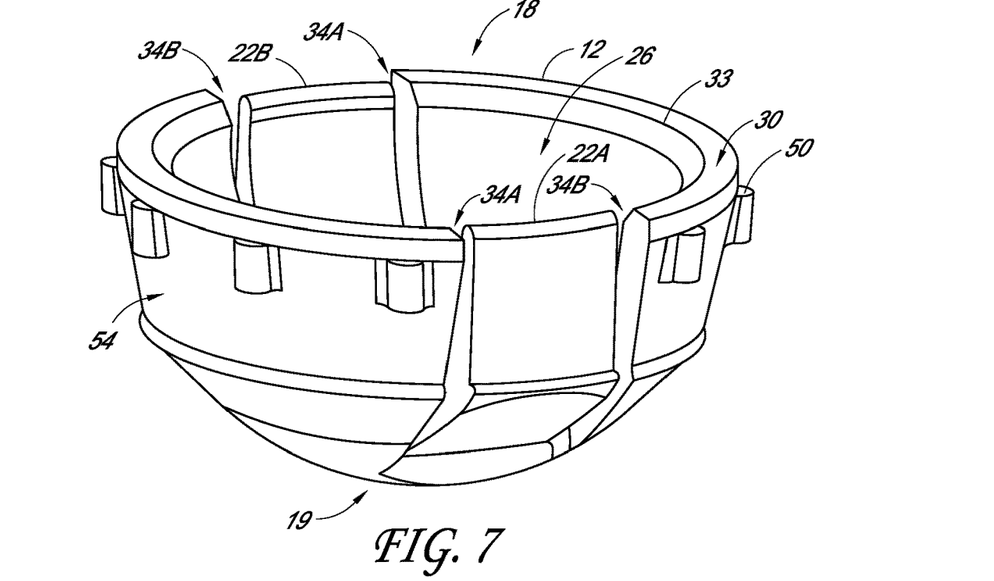
FIG. 7 is perspective view of an illustration of an example of another embodiment of a trial acetabular liner having two tabs disposed opposite each other.
Figure 8:
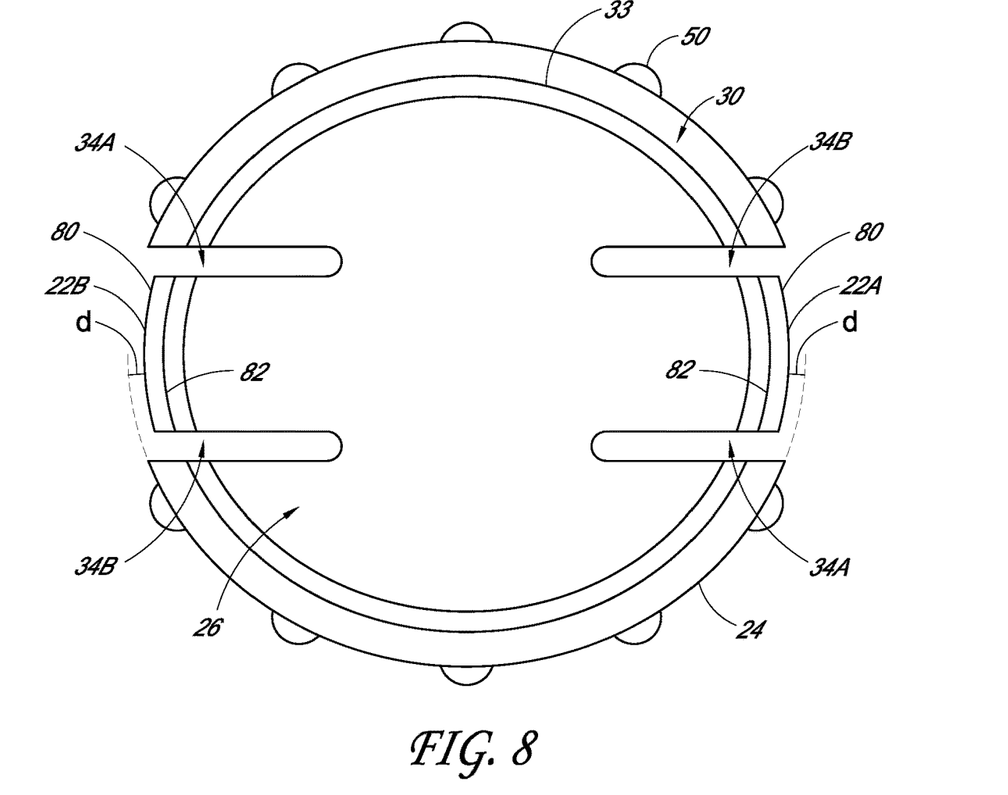
FIG. 8 depicts a plan view of the open end of the example of the acetabular liner in FIG. 7.

FIG. 7 and FIG. 8 illustrate another example of an embodiment of a trial acetabular liner 12. FIG. 7 is perspective view of the trial acetabular liner 12 embodiment. FIG. 8 depicts a plan view of the open end 18 of the trial acetabular liner 12 shown in FIG. 7. In this embodiment, the liner 12 include some of the same features as the liner illustrated in FIG. 2-5, for example, a first and second tab 22 disposed on opposite sides of the liner 12, an open an 18, a closed end 19, and an open end top surface 30, a distal peripheral edge 24, and an inner peripheral edge 33. Each of the tabs 22 is associated with a set of cutouts. In this embodiment, each set of cutouts includes a first cut out 34A and a second cutout 34B that extend all the way through liner in an axial direction, defining lateral edges of the tab 22, which allows the tabs 22 to move. Unlike the embodiment illustrated in FIGS. 2-5, the embodiment in FIGS. 7 and 8 does not include a third cutout 38 (FIG. 2). Also, each tab includes a single projection 28 running along the out surface of the tab 22, although in some embodiments of the trial acetabular liner illustrated in FIGS. 7 and 8, the tab 22 may have more than one projection, and also may have other features that are illustrated in the embodiment illustrated in FIG. 2, e.g., an indentation 32, a groove 46 etc.

Still referring to the embodiment in FIGS. 7 and 8, the outside edge 80 of the tab 22 is inset a distance "d" from the distal peripheral edge 24 of the liner 12, as illustrated in FIG. 7. That is, the outside edge 80 of the tab 22 is inset a distance "d" from where the distal peripheral edge 24 of the liner 12 would be if it continued in the same curve along to the tab 22. In some embodiments, distance d may be about (e.g., plus or minus 0.5 mm), 1 mm, 2 mm, 3 mm, 4 mm, 5 mm, 6 mm, 7 mm, 8 mm, 9 mm, or 10 mm. In some embodiments, distance d may be greater than 10 mm. In some embodiments, and as can be seen in FIG. 8, the inside edge 82 of the tab 22 corresponds to the curve in alignment of the inner peripheral edge 33 of the liner 12 such that a femoral head component received in the open end 18 of the liner 12 would contact the surface 26 on the interior wall of the liner 12. In some embodiments, the surface 26 is curved to conform with a curved exterior surface of the femoral head component in contact with the surface 26 for a smooth interaction of surfaces. The inset of the outside edge 80 allows a tool or the fingers of a user to engage tab 22 and move tab 22 two release the projection 28 from a locked position in a corresponding groove or indentation of a shell.

Various embodiments of an trail acetabular liner using one or more of the features described herein can be implemented. For example, in various examples of embodiment A, a trial acetabular liner, characterized as having defined perpendicular radial and axial directions, can include a closed first end, an open second end, and a liner wall extending between the closed first end and the open second end, the liner wall having a distal peripheral edge defining an outside perimeter of the open second end. The liner wall can include an interior surface defining a chamber for receiving a femoral head component, an exterior surface configured to be received within an acetabular shell, at least one set of cutouts. Each set of cutout can include a first cutout through a portion of the liner wall, a second cutout aligned to the first cutout and through the liner wall, the first and second cutouts extending from the distal peripheral edge into the interior surface of the liner, and a third cutout in the interior surface of the liner and partially through the liner wall, the third cutout extending from a proximal edge of the first cutout to a proximate edge of the second cutout, the proximate edges of the first and second cutouts nearer a center axis of the liner than the distal peripheral edge. The trail acetabular liner can further include at least one movable tab extending from the distal peripheral edge towards the center axis of the liner, each tab having sidewalls defined by one of the at least one set of cutouts, and each tab comprising at least one projection on an exterior surface of the tab configured to removably secure to a portion of an acetabular shell. In some examples of embodiment A of the trail acetabular liner, the first cutout is parallel to the second cutout. In some examples of embodiment A of the trail acetabular liner, the first cutout is not parallel to the second cutout, but instead are aligned non-parallel such that the first and second cutout are closer together near the third cutout and further apart at the distal peripheral edge (e.g., that defines the perimeter of the open second end.

In some examples of embodiment A of the trail acetabular liner, the at least one projection comprises a first projection and a second projection. In some examples of embodiment A with the first projection and second projection, the at least one tab further comprises a first indentation in the distal peripheral edge on the tab, the first indentation extending in the axial direction towards the closed first end from a first end of the first indention on the distal peripheral edge to a second end of the first indention proximate to the first and second projections. Further in some such examples, the first indentation defines a side portion of the first projection and a side portion of the second projection. In some examples of embodiment A of the trail acetabular liner, the liner includes a first movable tab and a second movable tab, the first movable tab and the second movable tab aligned opposite each other. In some of such examples, the at least one set of cutouts comprises a first set of cutouts associated with the first moveable tab and a second set of cutouts associated with the second moveable tab. In some examples of embodiment A having said first indentation, the at least one tab further comprises a liner wall groove beginning near the second end of the first indentation and extending towards the closed first end of the liner. In some further examples of such embodiments, the liner wall groove is separate from the indentation. In some further examples of such embodiments, the liner wall groove is separated from the first indentation by an edge at the second end of the first indentation. In some examples of embodiment A having a first indentation, the at least one tab further includes a second indentation extending axially from near the second end of the first indentation towards the first closed end of the liner, the second indentation being indented less than or the same amount as first indentation. In some examples of embodiments having a first indentation, the first indentation extends past the at least one projection. In some examples of embodiments having a first indentation, the first indentation is structured to receive a surface of a tool, and wherein the tab is configured to move inwardly in a direction towards an axis of the liner when force is applied to the first indentation by the tool. In some examples of embodiments having a first indentation, the first indentation is structured to receive a surface of a finger, and wherein the tab is configured to move inwardly in a direction towards axis of the liner when force is applied to the first indentation by the finger. In some embodiments of embodiment A of the trail acetabular liner, the third cutout is aligned perpendicular to the first and second cutouts. In some embodiments of embodiment A of the trail acetabular liner, the third cutout is curved.

Other embodiments having other features are contemplated. For example, in an embodiment B a trial acetabular liner for use in determining an implantable liner to use for replacement of a hip joint, characterized as having defined perpendicular radial and axial directions, can include a closed first end, an open second end, and a liner wall extending between closed first end and the open second end, liner wall comprising an interior surface and an exterior surface, and at least one set of cutouts. The at least one set of cutout can include a first cutout through the liner wall, a second cutout through the liner wall, and a third cutout in the interior surface of the liner wall partially through the liner wall extending from the first cutout to the second cutout. Examples of embodiment B can also include at least one movable tab extending from the peripheral edge inwardly towards an axial center of the liner and having sidewalls defined by one of the at least one set of cutouts, the tab comprising at least one projection on an exterior surface of the tab configured to removably secure to an indentation of an acetabular shell. In some examples of embodiment B of the trail acetabular liner, the at least one projection comprises a first projection and a second projection. In some examples of embodiment B of the trail acetabular liner the at least one tab further comprises a first indentation in the distal peripheral edge on the tab, the indentation extending in the axial direction towards the closed first end from a first end of the first indentation on the distal peripheral edge to a second end of the first indentation proximate to the first and second projections. In some examples of embodiment B having a first indentation, the first indentation defines a side portion of the first projection and a side portion of the second projection. In some examples of embodiment B, the at least one moveable tab comprises a first movable tab and a second movable tab disposed opposite each other. In some examples of embodiment B, the at least one set of cutouts comprises a first set of cutouts associated with the first moveable tab and a second set of cutouts associated with the second moveable tab. In some examples of embodiment B, the at least one tab further comprises a liner wall groove beginning near the second end of the first indentation and extending towards the closed first end of the liner. In some examples of embodiment B with a liner wall groove, the liner wall groove is separate from the first indentation. In such examples, the liner wall groove can be separated from the first indentation by an edge at the second end of the first indentation. In some examples of embodiment B, the at least one tab further includes a second indentation extending axially from near the second end of the first indentation towards the first closed end of the liner, the second indentation being indented less than or the same amount as first indentation. In some such examples of the trial acetabular liner, the first indentation extends past the at least one projection. In some examples of embodiment B of the trail acetabular liner, the first cutout is parallel to the second cutout. In some examples of embodiment B of the trail acetabular liner, third cutout is perpendicular to the first cutout and the second cutout. In some examples of embodiment B of the trail acetabular liner, third cutout is not perpendicular to the first cutout and the second cutout. In some examples of embodiment B of the trail acetabular liner, the third cutout is curved. In some examples of embodiments A or B of the trail acetabular liner, the first cutout and the second cutout are curved. In some examples of embodiment B of the trail acetabular liner, the first cutout is not parallel to the second cutout. In some examples of embodiment B of the trail acetabular liner, the third cutout is not perpendicular to the to the first cutout.

An embodiment C of a trial acetabular liner assembly can be characterized as having defined perpendicular radial and axial directions, and can include an acetabular shell and a liner. Examples of the liner of embodiment C can include a closed first end, an open second end, and a liner wall extending between closed first end and the open second end, the liner wall having a distal peripheral edge defining an outside perimeter of the open second end. The liner wall can include an interior surface defining a chamber for receiving a femoral head component, an exterior surface configured to be received within an acetabular shell, at least one set of cutouts including a first cutout through a portion of the liner wall, a second cutout aligned to the first cutout and through the liner wall, the first and second cutouts extending from the distal peripheral edge into the interior surface of the liner, and a third cutout in the interior surface of the liner and partially through the liner wall, the third cutout extending from a proximal edge of the first cutout to a proximate edge of the second cutout, the proximate edges of the first and second cutouts nearer a center axis of the liner than the distal peripheral edge, and at least one movable tab extending from the distal peripheral edge towards the center axis of the liner, each tab having sidewalls defined by one of the at least one set of cutouts, and each tab comprising at least one projection on an exterior surface of the tab configured to removably secure to a portion of the acetabular shell. In some examples, the first and second cutouts can be aligned parallel. In some examples, the first and second cutouts can be aligned an angle relative to each other. In some examples of any of embodiments A, B, or C, the first and second cutout can be aligned such that they are closer together near the third cutout, or can be aligned such that they are further apart near the third cutout, or aligned to be parallel. In some examples of embodiment C, the acetabular shell includes an inner surface having a groove configured to receive the at least one projection. In some examples of embodiment C, the inner surface of the acetabular shell further comprises at least one an indentation for receiving a locking portion of an implantable acetabular liner. In some examples of the trial acetabular liner assembly of embodiment C, the at least one projection on the exterior surface of the depressible tab is configured to snap-fit with the groove of the acetabular shell. In some examples of the trial acetabular liner assembly of embodiment C, the at least one projection comprises a first projection and a second projection, and wherein the first and second projections on the exterior surface of the depressible tab are configured to snap-fit with the groove on the inner surface of the acetabular shell.

The foregoing description details certain embodiments of the systems, devices, and methods disclosed herein. It will be appreciated, however, that no matter how detailed the foregoing appears in text, the systems, devices, and methods can be practiced in many ways. As is also stated above, it should be noted that the use of particular terminology when describing certain features or aspects of the invention should not be taken to imply that the terminology is being re-defined herein to be restricted to including any specific characteristics of the features or aspects of the technology with which that terminology is associated.

Conditional language such as, among others, "can," "could," "might" or "may," unless specifically stated otherwise, are otherwise understood within the context as used in general to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Headings are included herein for reference and to aid in locating various sections. These headings are not intended to limit the scope of the concepts described with respect thereto. Such concepts may have applicability throughout the entire specification.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

The phrase "based on" does not mean "based only on," unless expressly specified otherwise. In other words, the phrase "based on" describes both "based only on" and "based at least on." Unless otherwise explicitly stated, articles such as "a" or "an" should generally be interpreted to include one or more described items. Accordingly, phrases such as "a device configured to" are intended to include one or more recited devices.

It will be appreciated by those skilled in the art that various modifications and changes may be made without departing from the scope of the described technology. Such modifications and changes are intended to fall within the scope of the embodiments. It will also be appreciated by those of skill in the art that parts included in one embodiment are interchangeable with other embodiments; one or more parts from a depicted embodiment can be included with other depicted embodiments in any combination. For example, any of the various components described herein and/or depicted in the figures may be combined, interchanged or excluded from other embodiments.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention as embodied in the attached claims. Applicant reserves the right to submit claims directed to combinations and sub-combinations of the disclosed inventions that are believed to be novel and non-obvious. Inventions embodied in other combinations and sub-combinations of features, functions, elements and/or properties may be claimed through amendment of those claims or presentation of new claims in the present application or in a related application. Such amended or new claims, whether they are directed to the same invention or a different invention and whether they are different, broader, narrower or equal in scope to the original claims, are to be considered within the subject matter of the inventions described herein.

What is claimed is:

1. A trial acetabular liner defining perpendicular radial and axial directions, the trial acetabular liner comprising:
    a closed first end;
    an open second end; and
    a liner wall extending between the closed first end and the open second end, the liner wall having a distal peripheral edge defining an outside perimeter of the open second end, the liner wall comprising:
    an interior surface defining a chamber for receiving a femoral head component;
    an exterior surface configured to be received within an acetabular shell;
    at least one set of cutouts including
        a first cutout through a portion of the liner wall;
        a second cutout parallel to the first cutout and through the liner wall, the first and second cutouts extending from the distal peripheral edge into the interior surface of the liner, and
        a third cutout in the interior surface of the liner and partially through the liner wall, the third cutout extending from a proximal end of the first cutout to a proximal end of the second cutout, the proximal ends of the first cutout and the second cutout nearer a center axis of the liner than the distal peripheral edge of the liner wall;
    at least one movable tab extending from the distal peripheral edge towards the center axis of the liner, each of the at least one movable tabs associated with one of the at least one set of cutouts and having sidewalls defined by the associated set of cutouts, a distal wall and a proximal wall defined by the third cutout of the associated set of cutouts, the distal wall on the respective tab facing inwards towards an axis of the liner and facing the proximal wall on the opposite side of the third cutout, and each tab comprising at least one projection on an exterior surface of the tab configured to removably secure to a portion of an acetabular shell, the tab being movable through the third cutout such that the distal wall moves towards the proximal wall and disengages the at least one projection from the acetabular shell.

2. The acetabular liner of claim 1, wherein the at least one projection comprises a first projection and a second projection.

3. The acetabular liner of claim 2, wherein the at least one tab further comprises a first indentation in the distal peripheral edge on the tab, the first indentation extending in the axial direction towards the closed first end from a first end of the first indention on the distal peripheral edge to a second end of the first indention proximate to the first and second projections.

4. The acetabular liner of claim 3, wherein the first indentation defines a side portion of the first projection and a side portion of the second projection.

5. The acetabular liner of claim 3, wherein the at least one tab further comprises a liner wall groove beginning near the second end of the first indentation and extending towards the closed first end of the liner.

6. The acetabular liner of claim 5, wherein the liner wall groove is separate from the first indentation.

7. The acetabular liner of claim 6, wherein the liner wall groove is separated from the first indentation by an edge at the second end of the first indentation.

8. The acetabular liner of claim 3, wherein the at least one tab further includes a second indentation extending axially from near the second end of the first indentation towards the first closed end of the liner, the second indentation being indented less than or the same amount as first indentation.

9. The acetabular liner of claim 3, wherein the first indentation extends past the at least one projection.

10. The acetabular liner of claim 3, wherein the first indentation is structured to receive a surface of a tool, and wherein the tab is configured to move inwardly in a direction towards an axis of the liner when force is applied to the first indentation by the tool.

11. The acetabular liner of claim 3, wherein the first indentation is structured to receive a surface of a finger, and wherein the tab is configured to move inwardly in a direction towards axis of the liner when force is applied to the first indentation by the finger.

12. The acetabular liner of claim 1, wherein the at least one tab includes a first movable tab and a second movable tab, the first movable tab and the second movable tab aligned opposite each other.

13. The acetabular liner of claim 12, wherein the at least one set of cutouts comprises a first set of cutouts associated with the first moveable tab and a second set of cutouts associated with the second moveable tab.

14. The acetabular liner of claim 1, wherein the third cutout is aligned perpendicular to the first and second cutouts.

15. A trial acetabular liner for use in determining an implantable liner to use for replacement of a hip joint, comprising:
    a closed first end;
    an open second end; and
    a liner wall extending between the closed first end and the open second end, liner wall comprising an interior surface and an exterior surface;
    a first set of cutouts including
        a first cutout through the liner wall,
        a second cutout through the liner wall, and
        a third cutout in the interior surface of the liner wall partially through the liner wall extending from a proximal end of the first cutout to a proximal end of the second cutout, the third cutout aligned perpendicular to the first cutout and the second cutout;
    a movable first tab extending from the peripheral edge inwardly towards an axial center of the liner and having sidewalls defined by the set of cutouts, the first tab having a distal wall and a proximal wall defined by the third cutout, the distal wall facing inwards towards an axis of the liner and facing the proximal wall on the opposite side of the third cutout, the first tab comprising at least one projection on an exterior surface of the first tab configured to removably secure to an indentation of an acetabular shell, wherein the first tab is movable such that the distal wall moves through the space of the third cutout towards the proximal wall to disengage the at least one projection from the acetabular shell.

16. The acetabular liner of claim 15, wherein the at least one projection comprises a first projection and a second projection.

17. The acetabular liner of claim 15, wherein the first tab further comprises a first indentation in the distal peripheral edge on the first tab, the indentation extending in the axial direction towards the closed first end from a first end of the first indentation on the distal peripheral edge to a second end of the first indentation proximate to the first and second projections.

18. The acetabular liner of claim 17, further comprising a second movable tab disposed opposite the first tab.

19. The acetabular liner of claim 15, further comprising a second set of cutouts associated with the second moveable tab, the second set of cutouts including a first cutout through the liner wall, a second cutout through the liner wall, and a third cutout in the interior surface of the liner wall partially through the liner wall extending from a proximal end of the first cutout to a proximal end of the second cutout, the third cutout aligned perpendicular to the first cutout and the second cutout.

20. A trial acetabular liner assembly defining perpendicular radial and axial directions, the trial acetabular liner assembly comprising:
   an acetabular shell;
   a liner, comprising:
   a closed first end;
   an open second end; and
   a liner wall extending between the closed first end and the open second end, the liner wall having a distal peripheral edge defining an outside perimeter of the open second end, liner wall comprising:
   an interior surface defining a chamber for receiving a femoral head component;
   an exterior surface configured to be received within an acetabular shell;
   at least one set of cutouts including
      a first cutout through a portion of the liner wall;
      a second cutout parallel to the first cutout and through the liner wall, the first and second cutouts extending from the distal peripheral edge into the interior surface of the liner, and
      a third cutout in the interior surface of the liner and partially through the liner wall, the third cutout extending from a proximal end of the first cutout to a proximal end of the second cutout, the proximal ends of the first and second cutouts nearer a center axis of the liner than the distal peripheral edge;
   at least one movable tab extending from the distal peripheral edge towards the center axis of the liner, each tab having sidewalls defined by one of the at least one set of cutouts, a distal wall and a proximal wall defined by the third cutout and on opposite sides of the third cutout, and each tab comprising at least one projection on an exterior surface of the tab configured to removably secure to a portion of the acetabular shell, wherein the first tab is movable such that the distal wall moves through the third cutout towards the proximal wall to disengage the at least one projection from the acetabular shell.

* * * * *

UNITED STATES PATENT AND TRADEMARK OFFICE
CERTIFICATE OF CORRECTION

| | | |
|---|---|---|
| PATENT NO. | : 11,103,367 B2 | Page 1 of 1 |
| APPLICATION NO. | : 16/782721 | |
| DATED | : August 31, 2021 | |
| INVENTOR(S) | : Wills et al. | |

It is certified that error appears in the above-identified patent and that said Letters Patent is hereby corrected as shown below:

On the Title Page

Item (71), Applicant, Line 1, delete "Encore Medical, L.P.," and insert --Encore Medical, L.P. (d/b/a DJO Surgical),--.

Item (73), Assignee, Line 1, delete "Encore Medical, L.P.," and insert --Encore Medical, L.P. (d/b/a DJO Surgical),--.

Item (60), Related U.S. Application Data, Line 1, delete "Dec." and insert --Feb.--.

In the Specification

In Column 3, Line 54, delete "to the to the" and insert --to the--.

In Column 11, Line 4, delete "and or" and insert --and/or--.

In Column 12, Line 35, delete "FIG." and insert --FIGS.--.

In Column 12, Line 40, delete "cut out" and insert --cutout--.

In Column 15, Line 23, delete "to the to the" and insert --to the--.

Signed and Sealed this
Twenty-eighth Day of December, 2021

Drew Hirshfeld
*Performing the Functions and Duties of the*
*Under Secretary of Commerce for Intellectual Property and*
*Director of the United States Patent and Trademark Office*